(12) United States Patent
Michaeli et al.

(10) Patent No.: US 11,474,174 B2
(45) Date of Patent: Oct. 18, 2022

(54) SYSTEMS AND METHODS FOR UTILIZING PERIODIC IRRADIATION TO ENHANCE SENSITIVITY OF MAGNETIC RESONANCE DETECTION

(71) Applicant: REGENTS OF THE UNIVERSITY OF MINNESOTA, Minneapolis, MN (US)

(72) Inventors: Shalom Michaeli, Minneapolis, MN (US); Timo Liimatainen, Minneapolis, MN (US); Hanne Laakso, Minneapolis, MN (US); Silvia Mangia, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 63 days.

(21) Appl. No.: 17/008,286

(22) Filed: Aug. 31, 2020

(65) Prior Publication Data

US 2021/0063512 A1 Mar. 4, 2021

Related U.S. Application Data

(60) Provisional application No. 62/894,279, filed on Aug. 30, 2019.

(51) Int. Cl.
*G01R 33/36* (2006.01)
*G01R 33/56* (2006.01)
(Continued)

(52) U.S. Cl.
CPC .......... *G01R 33/3607* (2013.01); *A61B 5/055* (2013.01); *G01R 33/385* (2013.01); *G01R 33/4828* (2013.01); *G01R 33/5608* (2013.01)

(58) Field of Classification Search
CPC .............. G01R 33/3607; G01R 33/385; G01R 33/4828; G01R 33/5608
See application file for complete search history.

(56) References Cited

U.S. PATENT DOCUMENTS 7,932,719 B2 4/2011 Liimatainen et al.
8,723,518 B2 5/2014 Seiberlich et al.
(Continued)

OTHER PUBLICATIONS

Liimatainen, Timo, et al. "Relaxation along fictitious field (RAFF) contrast in bovine articular cartilage." Proceedings of the 18th Annual Meeting of ISMRM. 2010. (Abstract).
(Continued)

*Primary Examiner* — Gregory H Curran
(74) *Attorney, Agent, or Firm* — Quarles & Brady LLP

(57) ABSTRACT

The present disclosure provides a method for using a magnetic resonance system to measure magnetization data from a region of interest in a subject having a spin system that includes at least a first labile spin species and a second labile spin species experiencing chemical exchange. The method includes applying periodic radiofrequency irradiation to the spin system using a frequency swept pulse sequence having frequency and amplitude modulation functions, wherein sweeping a frequency of the RF irradiation together with amplitude modulation generates a magnetic field component having an effective field. The method further includes generating off resonance side bands in a frequency domain positioned adjacent the resonant frequency of the first labile spin species or the second labile spin species by applying the periodic RF irradiation to induce the instantaneous flip of the effective field with periodicity of RF irradiation tuned to the chemical shift difference of the exchanging sites.

21 Claims, 10 Drawing Sheets

(51) Int. Cl.
      *A61B 5/055*     (2006.01)
      *G01R 33/48*     (2006.01)
      *G01R 33/385*     (2006.01)

(56)            References Cited

U.S. PATENT DOCUMENTS

| | | |
|---|---|---|
| 9,222,999 B2 | 12/2015 | Michaeli et al. |
| 2012/0286780 A1* | 11/2012 | Michaeli ............... G01R 33/446 |
| | | 324/309 |
| 2015/0301141 A1 | 10/2015 | Griswold et al. |
| 2016/0278661 A1* | 9/2016 | Griswold ............... A61B 5/004 |

OTHER PUBLICATIONS

Demetriou, Eleni, et al. "High rotating frame relaxation MRI mapping for detecting ischemia in rats." Proc. Intl. Soc. Mag. Reson. Med. 26 (2018) 5025.

* cited by examiner

SYSTEMS AND METHODS FOR UTILIZING PERIODIC IRRADIATION TO ENHANCE SENSITIVITY OF MAGNETIC RESONANCE DETECTION

CROSS-REFERENCES TO RELATED APPLICATIONS

This application claims the benefit of and priority to U.S. Patent Application No. 62/894,279, filed Aug. 30, 2019, the contents of which are incorporated herein by reference.

STATEMENT REGARDING FEDERALLY SPONSORED RESEARCH

Not applicable

BACKGROUND

MRI is an increasingly sensitive molecular imaging platform for visualizing, characterizing, and measuring biological processes at the molecular and cellular levels in humans. Detection of metabolites and biologically active electrolytes has been a major driving force in the emergence of in vivo magnetic resonance (MR) imaging and/or spectroscopy methods employing $^1$H as well as low-$\gamma$ nuclei such as $^{31}$P and $^{23}$Na. These methods indeed permit access to some of the most critical metabolites and ions that enable cellular function and that are thus linked to dysfunction induced by disease states. However, such MR applications are generally hampered by sensitivity limitations due to the relatively low concentrations of target metabolites in the region of interest and/or the inherently low sensitivity of low-$\gamma$ nuclei.

MRI can be used to measure the exchange of magnetization between molecules to provide unique information about the chemical and molecular environment of samples or tissues. One type of such exchange measurement is broadly referred to in the field as magnetization transfer. This technique is capable of measuring the exchange of magnetization from spin species that have short transverse relaxation times ($T_2$) and can capture exchange between two- and multiple pools undergoing exchange. However, because many different pools may have short $T_2$, this technique is not particularly specific.

Another type of magnetization exchange occurs between water protons and a molecule with long enough $T_2$ that its difference in frequency from water can be observed. Saturation of the magnetization from this molecule will generally decrease the measurable signal from water. This effect is generally referred to in the field as chemical exchange saturation transfer ("CEST"). Two different types of molecules can generate CEST effects: endogenous, or naturally occurring, molecules and exogenous contrast agents. In either instance, the molecules whose chemical exchange with water produces the CEST effect are generally referred to as so-called "exchangeable protons."

A number of different molecular groups have been suggested for CEST studies, such as functional groups containing —OH, —NH$_2$, or —NRH. Labile protons such as these can be selectively saturated by an RF pulse, and the saturation subsequently transferred to the bulk water signal via proton chemical exchange. CEST imaging has been demonstrated in mapping low-concentration metabolites such as creatine (Cr), glucose, glutamate, and changes in microenvironment properties such as temperature and pH, promising a host of in vivo applications such as imaging of ischemic stroke and tumor.

CEST MRI suffers from several limitations including long image acquisition times and the qualitative nature of the CEST contrast, which depends on many factors, including the chemical exchange rate, concentration of exchangeable protons, longitudinal relaxation time, and RF saturation power. Additionally, CEST is sensitive to the strength of the magnetic field ($B_0$) because susceptibility variations increase with magnetic field. One needs to know $B_0$ accurately in order to radiate the chemical species to get a desired response. Further, CEST uses continuous waves (CW) of irradiation, which increases SAR when increasing sensitivity. Finally, in vivo CEST quantification remains challenging due to concomitant effects such as RF spillover (direct water saturation), semisolid macromolecular magnetization transfer (MT) and nuclear Overhauser effects (NOE).

Currently, there is a need in the art for developing improved techniques for probing spin systems coupled by specific processes, such as exchange between spins with different chemical shifts, and for separating exchange relaxation channel from dipolar relaxation pathway.

SUMMARY OF THE DISCLOSURE

The present disclosure addresses the aforementioned drawbacks by providing a new paradigm for measuring magnetization data, such as exchange-induced relaxation rate constants for characterization of tissue properties. Unlike CEST, which is sensitive to the strength of the magnetic field ($B_0$) and has a high specific absorption rate (SAR), some aspects of the present disclosure provide a technique that is insensitive to $B_0$ and provide a significantly reduced SAR due to some embodiments utilizing low average flip angles and low radio frequency powers. Further, as compared to CEST, the present disclosure does not require two opposite spectral location measurements, rather some embodiments of the present disclosure allow for measurement of magnetization data using a single acquisition.

Some aspects of the present disclosure provide a method for using a magnetic resonance (MR) system to measure magnetization data from a region of interest in a subject having a spin system that includes at least a first labile spin species and a second labile spin species experiencing chemical exchange. The method includes applying periodic radiofrequency (RF) irradiation to the spin system using a frequency swept pulse sequence having frequency and amplitude modulation functions, where sweeping a frequency of the RF irradiation together with amplitude modulation generates a magnetic field component having an effective field. The method further includes generating off resonance side bands in a frequency domain positioned adjacent the resonant frequency of the first labile spin species or the second labile spin species by instantaneously flipping the effective field when applying the periodic RF irradiation, and acquiring magnetization data corresponding to at least one of the off resonance side bands.

In some aspects, the present disclosure provides a method for measuring magnetization data using a magnetic resonance (MR) system from a region of interest in a subject having a spin system that includes at least a first labile spin species and a second labile spin species experiencing chemical exchange. The method includes applying periodic radiofrequency (RF) irradiation to a spin system in a subject using a frequency swept pulse sequence having frequency and amplitude modulation functions, where the frequency swept pulses are configured to generate spin relaxation in the presence of a fictitious field in a second rotating frame of reference based on at least one magnetic field component that arises based on an effective field in a first rotating frame of reference, wherein the second rotating frame of reference is of a higher order than the first rotating frame of reference, and wherein each different rotating frame is associated with an effective field. The method also includes generating off resonance side bands in a frequency domain positioned adjacent the resonant frequency of the first labile spin species or the second labile spin species by applying the periodic RF irradiation to induce an instantaneous flip of the effective field with a periodicity of the pulse sequence tuned to a chemical shift difference between exchanging sites, and acquiring magnetization data corresponding to at least one of the off resonance side bands.

In some aspects, the present disclosure provides a method for measuring magnetization data using a magnetic resonance (MR) system from a region of interest in a subject having a spin system that includes at least a first labile spin species and a second labile spin species experiencing chemical exchange. The method includes applying periodic radiofrequency (RF) irradiation to the spin system using a pulse sequence having amplitude and frequency modulated pulses. The method further includes generating off resonance side bands in a frequency domain positioned adjacent the resonant frequency of the first labile spin species or the second labile spin species by applying the periodic RF irradiation. When the magnetization is tipped to a selected tip angle, the instantaneous flip of the effective field is induced. In some embodiments, the period of the RF irradiation is selected to correspond to a chemical shift difference between the first resonant species and the second resonant species. The method also includes acquiring magnetization data corresponding to at least one of the off resonance side bands.

In further aspects of the present disclosure, a magnetic resonance imaging (MRI) system is provided that includes a magnet system configured to generate a polarizing magnetic field about a portion of a subject positioned in the MRI system, a plurality of gradient coils configured to apply a gradient field to the polarizing magnetic field, a radio frequency (RF) system configured to apply a RF excitation field to the subject, and acquire there from a set of magnetic resonance image (MRI) data and at least one processor. The at least one processor is configured to control the RF system to apply periodic RF irradiation to a region of interest in the subject using a frequency swept pulse sequence having frequency and amplitude modulation functions to excite a spin system in the region of interest that includes at least a first labile spin species and a second labile spin species experiencing chemical exchange. Sweeping a frequency of the RF irradiation together with amplitude modulation generates a magnetic field component having an effective field. The at least one processor is also configured to control the plurality of gradient coils and the RF system to generate off resonance side bands in a frequency domain positioned adjacent a resonant frequency of the first labile spin species or the second labile spin species by applying the periodic RF irradiation to induce an instantaneous flip of the effective field at frequency of periodic irradiation which generates side bands matched to the chemical shift difference between exchanging sites. The at least one processor is further configured to control the plurality of gradient coils and the RF system to acquire magnetization transfer data from the subject corresponding to at least one of the off resonance side bands.

In some aspects, the present disclosure provides a method for generating a tissue property in a subject using magnetic resonance fingerprinting (MRF). The method includes acquiring MRF data from a region of interest in a subject by performing a pulse sequence having a series of varied sequence blocks to elicit signal evolutions, where the varied sequence blocks include a frequency swept or spin lock pulse sequence configured to generate spin relaxation in the presence of an effective field in a relaxation along a fictitious field in a rotating from of rank n (RAFFn), where n ranges from 2 to 5 (e.g., from 2 to 3, or from 2 to 4, or from 2 to 5, or from 3 to 4, or from 3 to 5, or from 4 to 5). The method further includes comparing the MRF data to an MRF dictionary to generate the tissue property from the region of interest.

In some aspects, the method includes varying the flip angle within the varied sequence block, where the flip angle may be varied from 1° to 89°.

In some aspects, the method includes varying exchanging site values (e.g., $P_A$ and $P_B$) within the varied sequence block.

In some aspects, the method includes varying chemical shift difference values between exchanging sites $\Delta\omega$ within the varied sequence block.

In some aspects, the method includes fitting the acquired MRF data pixel-by-pixel to simulated values in the MRF dictionary to identify a match. In some aspects, the parameters associated with the tissue property are extracted from the signal evolution in the match. In some aspects, the tissue property values are utilized to generate a tissue property map of the region of interest of the subject.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are methods of using a magnetic resonance (MR) system for measuring magnetization data from a region of interest in a subject. As stated above, conventional MR techniques for measuring magnetization transfer data, such as CEST, suffer from several limitations, such as sensitivity to the strength of the magnetic field ($B_0$) due to susceptibility variations and long acquisition times attributed, in part, to the use of continuous waves (CW) of irradiation and the requirement to acquire two opposite spectral location measurements.

Unlike CEST, some aspects of the present disclosure provide a technique that is insensitive to the strength of the magnetic field ($B_0$) and provide a significantly reduced SAR. Further, as will be described, the present disclosure does not require two opposite spectral location measurements, and may be performed in a single acquisition.

Figure 1:
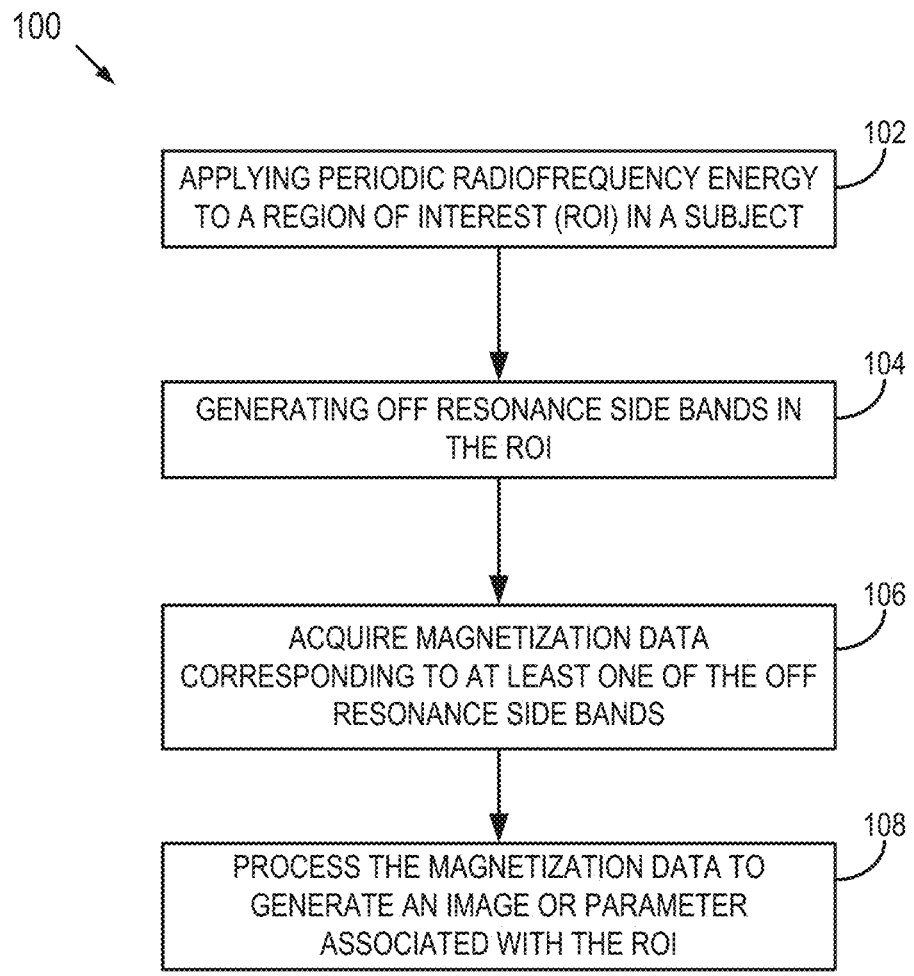
FIG. 1 is a flowchart setting forth the steps of a method for acquiring MR signal from exchanging system in accordance with an embodiment described in the present disclosure.

Referring now to FIG. 1, a flowchart is illustrated as setting forth the steps of an example method 100 for measuring magnetization data from a region of interest in a subject using a magnetic resonance (MR) system. As indicated by step 102, the method 100 includes applying periodic radiofrequency (RF) irradiation to a spin system in the region of interest having at least a first labile spin species and a second labile spin species experiencing chemical exchange (e.g., protons exchanging between two chemical functional groups). Exemplary labile spin species include metabolites or chemical moieties having functional groups including, but not limited to, an amide (—NH), amine (NH$_2$), hydroxyl (—OH), carboxyl (—COOH), and/or a thiol (—SH).

In some embodiments, the step of applying periodic RF irradiation 102 includes applying periodic RF irradiation to the spin system in the form of a frequency swept pulse sequence. The frequency swept pulse sequence may be configured with at least one frequency and/or amplitude modulation function. By sweeping the frequency of the RF pulse together with amplitude modulation under non-adiabatic conditions, a fictitious RF field component is created having an effective field with an amplitude that differs from that under an adiabatic condition.

In some embodiments, as indicated by step 104, the method 100 further includes generating off resonance side bands that are positioned adjacent to the resonant frequency of the first labile spin species and/or the second labile spin species. In some embodiments, the off resonance side bands may be generated by applying a periodic frequency swept pulse sequence having frequency and amplitude modulation function. In some embodiments, off resonance side bands may be produced by applying frequency swept pulse sequences having relatively small tip angles of magnetization (i.e., less than 45° or between 0.1° and 45°). Additionally or alternatively, off resonance side bands may be generated by applying the periodic RF irradiation when magnetization is tipped to a selected angle and the period of irradiation is set such the side bands is generated at the chemical shift of the exchanging sites. In some embodiments, suitable tip angles of magnetization for the frequency swept pulse sequences may range between about 0.1° to 45°. In some embodiments, the tip angles of magnetization are at least 0.1°, or at least 1°, or at least 2°, or at least 3°, or at least 4°, or at least 5°, or at least 6°, or at least 7°, or at least 8°, or at least 9°, or at least 10°, or at least 15°, or at least 20°, to less than 25°, or less than 30°, or less than 35°, or less than 40°, or less than 45°.

In some embodiments, the instantaneous flip of the effective field occurs when periodic RF irradiation is applied to the spin system such that the magnetization evolves in a single hemisphere, such as a positive or a negative hemisphere without undergoing inversion.

Referring back to FIG. 1, as indicated by step 106, the method 100 further includes acquiring magnetization data corresponding to at least one of the off resonance side bands. The magnetization data may be acquired and processed, as indicated by step 108, to yield an image, information, and/or parameters associated with biochemical data in the region of interest. The biochemical information and/or parameters may include, but are not limited to, a concentration of one or more metabolite, metabolic turnover, disposition kinetics, physiological parameters including intra-cellular pH, energy states of the region, and oxygen supply.

In some embodiments, suitable periodic frequency swept pulse sequences include, but are not limited to, hyperbolic secant pulse sequences, cosine pulse sequences, sine pulse sequences, Tan pulse sequences, Tanh pulse sequences, and linear function, each having frequency and amplitude modulation functions, and amplitude and frequency modulated pulses that induce relaxations in high rotating frames of rank n, such as Relaxation Along a Fictitious Field in the rotating frame of rank n (RAFFn).

Mathematically, the theory of performing RAFFn may be explained, without limiting the disclosure, as follows. For obtaining time-invariant and equal amplitudes and frequency components in the first rotating frame (n=1), the amplitude $\omega_1^{(1)}$ and frequency $\Delta\omega^1$ modulation functions in the first rotating frame of reference are defined as follows:

$$\omega_1^{(1)} = \tan\alpha_1 \omega_1^{max} \quad (1)$$

$$\Delta\omega^1 = \omega_1^{max} \quad (2)$$

where $\omega_1^{max}$ is the peak RF amplitude in rad/s and $\alpha_1$ is defined angle. The recursive relationship which was used for amplitude and frequency modulation of RAFFn for n>1 based on sine/cosine functions are given by:

$$\omega_1^{(n)}(t) = \Delta\omega_1^{(n-1)}(t)\sin(\int\omega_1^{(n-1)}(t)dt) \quad (3)$$

$$\Delta\omega^{(n)}(t) = \Delta\omega_1^{(n-1)}(t)\cos(\int\omega_1^{(n-1)}(t)dt) \quad (4)$$

For n=2, 4, 6 . . . and $$\omega_1^{(n)}(t) = \omega_1^{(n-1)}(t)\sin(\int\Delta\omega_1^{(n-1)}(t)dt) \quad (5)$$

$$\Delta\omega^{(n)}(t) = \omega_1^{(n-1)}(t)\cos(\int\Delta\omega_1^{(n-1)}(t)dt) \quad (6)$$

For n=3, 5, 7 . . . . . The pulse duration ($T_p$) is calculated as $4\pi/(\sqrt{2}\omega_1^{max})$. In some embodiments, each sine/cosine pulse consists of four RAFFn pulse elements treated according to a refocusing scheme. The average flip angle during the pulse may be estimated by calculating the flip angle of magnetization from the Z axis of the laboratory frame in each pulse point using Bloch equations and averaging the angle over the duration of the pulse.

In some embodiments, Bloch-McConnell formulation may be used to measure the relaxation during RAFFn. Relaxations during RF irradiation due to the dipolar interactions (like spins) are induced by anisochronous exchange between two pools A and B with different chemical shifts can be described using Bloch-McConnell equations written in the phase-modulated rotating frame, illustrated as follows:

$$\frac{dM_Z^A(t)}{dt} = \frac{M_0^A - M_Z^A(t)}{T_{1A}} - k_{ex}^{AB}M_Z^A(t) + \quad (7)$$
$$k_{ex}^{BA}M_Z^B(t) + \omega_1\sin(\phi)M_X^A(t) - \omega_1\cos(\phi)M_Y^A(t);$$

$$\frac{dM_Z^B(t)}{dt} = \frac{M_0^B - M_Z^B(t)}{T_{1B}} - k_{ex}^{BA}M_Z^B(t) + \quad (8)$$
$$k_{ex}^{AB}M_Z^A(t) + \omega_1\sin(\phi)M_X^B(t) - \omega_1\cos(\phi)M_Y^B(t);$$

$$\frac{dM_X^A(t)}{dt} = \quad (9)$$
$$-\frac{M_X^A(t)}{T_{2A}} - k_{ex}^{AB}M_X^A(t) + k_{ex}^{BA}M_X^B(t) + \Delta_A M_Y^A(t) - \omega_1\sin(\phi)M_Z^A(t);$$

$$\frac{dM_X^B(t)}{dt} = \quad (10)$$
$$-\frac{M_X^B(t)}{T_{2B}} - k_{ex}^{BA}M_X^B(t) + k_{ex}^{AB}M_X^A(t) + \Delta_B M_Y^B(t) - \omega_1\sin(\phi)M_Z^B(t);$$

$$\frac{dM_Y^A(t)}{dt} = \quad (11)$$
$$-\frac{M_Y^A(t)}{T_{2A}} - k_{ex}^{AB}M_Y^A(t) + k_{ex}^{BA}M_Y^B(t) - \Delta_A M_X^A(t) + \omega_1\cos(\phi)M_Z^A(t);$$

$$\frac{dM_Y^B(t)}{dt} = \quad (12)$$
$$-\frac{M_Y^B(t)}{T_{2B}} - k_{ex}^{BA}M_Y^B(t) + k_{ex}^{AB}M_Y^A(t) - \Delta_B M_X^B(t) + \omega_1\cos(\phi)M_Z^B(t);$$

where $\Delta_{A,B}$ are the chemical shifts in rad/s of exchanging groups A and B, respectively ($\delta\omega = |\Delta_A - \Delta_B|$), $k_{ex}^{AB} = P_B/\tau_{ex}$, and $$k_{ex}^{BA} = P_A/\tau_{ex}$$

are the exchange rate constants for exchanging site populations $P_A$ and $P_B$, and $T_{1,2,A,B} = 1/R_{1,2,A,B}$ an are the relaxation time constants at sites A and B, respectively. The longitudinal $R_1$ and transverse $R_2$ free precession relaxation rate constants may be calculated by considering dipolar interactions between isolated identical spins:

$$R_1 = \frac{3}{10}b^2\left(\frac{\tau_c}{1+\tau_c^2\omega_0^2} + \frac{4\tau_c}{1+4\tau_c^2\omega_0^2}\right); \quad (13)$$

$$R_2 = \frac{3}{20}b^2\left(3\tau_c + \frac{5\tau_c}{1+\tau_c^2\omega_0^2} + \frac{2\tau_c}{1+4\tau_c^2\omega_0^2}\right); \quad (14)$$

where $\tau_c$ is the rotational correlation time, $\omega_0$ is the Larmor precession frequency $$b = -\frac{\mu_0 \hbar \gamma^3}{4\pi r^3},$$

$\mu_0$ is vacuum permeability, $\hbar$ is Planc's constant, $\gamma$ is gyromagnetic ratio, and r is a hydrodynamic radius. To illustrate the methods provided herein, simulations of the two-site exchange are carried out using Equations 3-4. For the simulations, the calculations are performed with $R_1$ and $R_2$ obtained using Equations 5-12, with $\tau_c = 2 \cdot 10^{-12}$ s for both sites A and B. The decay of M ($M_0 = [0\ 0\ 1]$) during the pulse may be estimated by solving partial differential Equations 3-4 using, for example, a Runge-Kutta numerical method. Simulations are repeated for initially inverted magnetization $M_0 = [0\ 0\ -1]$ including steady state formation. In some embodiments, RAFFn pulses operate in the positive hemisphere, where the application of RAFFn pulse trains leads to a formation of steady state where the magnetization is not perturbed. In some embodiments, using a combined analysis of the signal evolution from positive +z and negative −z results in improved estimation of the relaxation rate constants during RAFFn.

Referring to FIGS. 2-7, simulations are conducted using Bloch-McConnell simulations to demonstrate the methods according to some aspects of the present disclosure. For the simulations presented herein, full set of two-pool Bloch-McConnell equations (e.g., Equations 5-10) are used, where $T_1$ and $T_2$ of the pools are calculated using the model of dipolar interaction between isolated spins using $\tau_c = 76 \cdot 10^{-12}$ s in Equations 5-12. The simulations are performed for water using a magnetic field of 9.4T with $^1$H gyromagnetic ratio of 42.576 MHz/T, Planck's constant of $1.054571628 \cdot 10^{-34}$ Js, hydrodynamic radius of $158 \cdot 10^{-12}$ m, and permeability of vacuum of $4\pi \cdot 10^{-7}$. The $T_1$ and $T_2$ were identical for both pools. Spin populations of the pools are set to $P_A = 0.1$ and $P_B = 1 - P_A$ and $\tau_{ex}$ is let to vary.

A coalesced exchange peak is assumed for the simulations disclosed herein, so that off-resonance for spin pool A is $\Delta_A = 2\pi P_B \cdot [0\ 6\ 12\ \ldots\ 3000]$ rad/s, and similarly for $\Delta_B = 2\pi P_A \cdot [0\ 6\ 12\ \ldots\ 3000]$ rad/s. In the exemplary RAFFn simulations, n is configured to be between 1 and 5, $\alpha_1$ is 45°, and $\omega_1^{max} = 2\pi \cdot 625$ rad/s, if not otherwise stated. When $\omega_1^{max}$ is set in Eq. (1), the maximum amplitude of RAFFn pulse decreases with increasing n and is dependent on $\alpha_1$. The number of points in waveform with refocusing scheme $PP_\pi^{-1}P_\pi P^{-1}$ is 128, the refocused pulse duration $$T_P = \frac{4\pi}{\sqrt{2}\,\omega_1^{max}}$$

giving 18 µs time increment between simulation points. 64 pulses were added into pulse train resulting up to 144 ms long irradiation.

Simulation of evolution of magnetization is performed in Matlab (Mathworks Inc.) by solving Bloch-McConnell equations by numerical partial differential equation solver (ode45, Matlab R2015a) time point-by-time point fashion. The solver calculated the evolution of magnetization in several variable size sub-points between the points giving an extra confidence for magnetization evolution. The time points 0 and 32 points evenly distributed within 144 ms are used to calculate relaxation rates from the simulated z-magnetizations. The z-magnetizations from both pools are summed up, and exponential decay taking into account steady state formation is fitted to data points by using, for example, non-linear least square fitting routine, unless otherwise stated.

Figure 2:
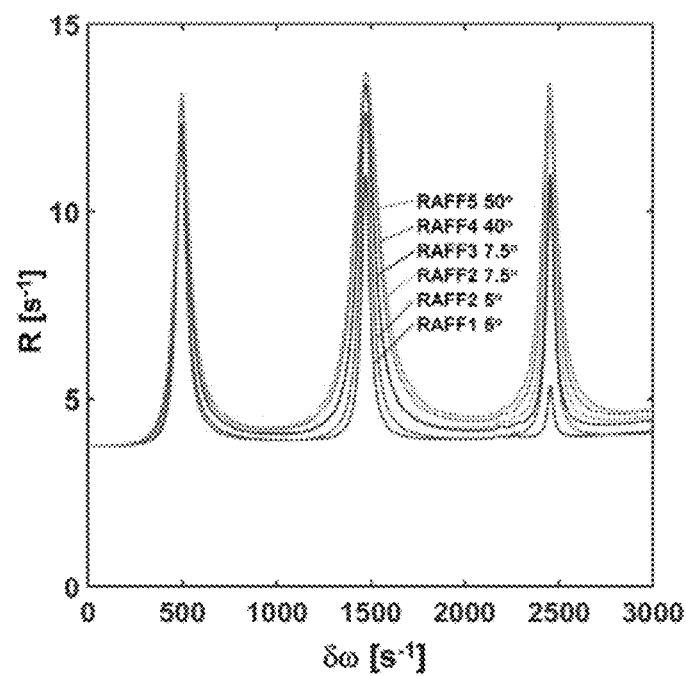
FIG. 2 is graph illustrating exchange-induced relaxation rate constants during periodic irradiation of RAFFn, where n=1-5 and RAFFn has a pulse duration of 2.3 ms in accordance to some aspects of the present disclosure. Average flip angle during the pulses is adjusted close to 5° leading to following actual pulse peak amplitudes (RAFF1 5.04° 55 Hz, RAFF2 3.82° 125 Hz, RAFF2 5.75° 186 Hz, RAFF3 4.94° 150 Hz, RAFF4 4.92° 273 Hz, and RAFF5 4.86° 249 Hz).

To demonstrate the effect of RF-pulse waveform on the relaxation rates over the range of different chemical shifts, frequency swept RF pulses with different amplitude and phase modulations are performed using the exemplary simulations. Referring to FIG. 1, exchange-induced relaxation rate constants during periodic irradiation of RAFFn, (n=1 to 5) are investigated where the average flip angle during the periodic irradiation is held close to 5° leading to the following actual pulse powers (e.g., RAFF 1 having a flip angle of 5.04° and pulse power of 55 Hz, RAFF2 having a flip angle of 3.82° and pulse power of 125 Hz, RAFF2 having a flip angle of 5.75° and pulse power of 186 Hz, RAFF3 having a flip angle of 4.94° and pulse power of 150 Hz, RAFF4 having a flip angle of 4.92° and pulse power of 273 Hz, and RAFF5 having a flip angle of 4.86° and pulse power of 249 Hz) by altering $\alpha_1$ in Eq. (1) for RAFF1-5. As shown in FIG. 2, RAFF2 is repeated with two different $\alpha_1$. Exchange correlation times of 10 ms, $P_A = 0.1$, and $\tau_c = 76 \cdot 10^{-12}$ s for both sites are used.

FIG. 2 shows an increase of the relaxation rate constants as the n in RAFFn increases. FIG. 2 further illustrates that the increased relaxation rate constants are found at the same chemical shift differences δω with different n, and appeared in the shapes of well-defined peaks. The relaxation rate at δω=1500 Hz increased gradually from 10.9 s$^{-1}$ with RAFF1 to 13.7 s$^{-7}$ with RAFF5. The full-width-half-maximum (FWHM) of the relaxation rate peak increased from 52 Hz with RAFF1 to 173 Hz with RAFF5. An increase of relaxation rate constant with RAFF5 at δω=1500 Hz can be explained by different contributions of the $T_{1\rho}$ and $T_{2\rho}$ relaxation channels, which were shown to provide different weightings in RAFFn.

These contributions vary with the tip angle of magnetization relatively to z axis of the laboratory frame. More complex amplitude and phase modulation functions of RAFF5 as compared to RAFF1 are responsible for the gradual increase of FWHM from RAFF1 to RAFF5. The analyses of the signal decay are based on single exponential fitting, which described sufficiently well the magnetization decay. The slight oscillations are observed when the relaxation reaches the maximal values, which corresponded to the peaks of the rate constants. Although this is the deviation from monoexponentiality, due to its minor oscillatory behavior the signal still is treated using monoexponential approximation.

Figure 3:
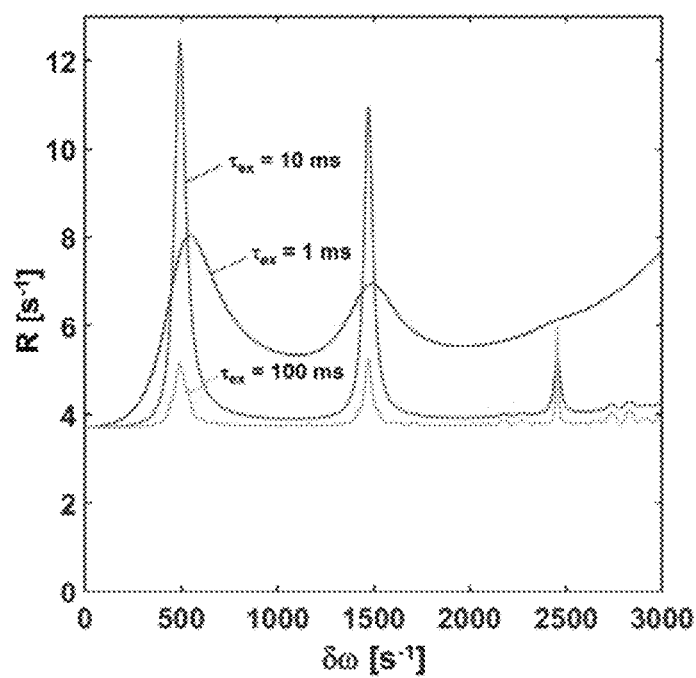
FIG. 3 is a graph of exchange-induced relaxation rate constants dependence on exchange correlation time between the sites A and B. For simulations, amplitude and phase modulated RF waveform of RAFF1 pulse are used, RAFF1 pulse duration is 2.3 ms, $\omega_1^{max}$=625 Hz, $\alpha_1$=5°, leading to actual pulse power of 55 Hz, PA=0.1, and the dipolar correlation time $\tau_c$=76·$10^{-12}$ s for both sites were used. Exchange correlation times are 1 ms, 10 ms and 100 ms as indicated on the plot.

Referring to FIG. 3, an exemplary simulation demonstrates that the exchange induced relaxation rate constant is dependent on exchange correlation times between sites A and B. The simulation demonstrates that the relaxation effect of periodic irradiation is more effective for relatively slow correlation times (i.e., 10 and 100 ms) for the pulse sequence settings presented in the simulation. An increase of the rate constants is observed when the system moves to the fast exchange regime, as it could be seen for the case of $\tau_{ex} = 1$ ms, with further broadening of the side bands 300-700 Hz.

Figure 4:
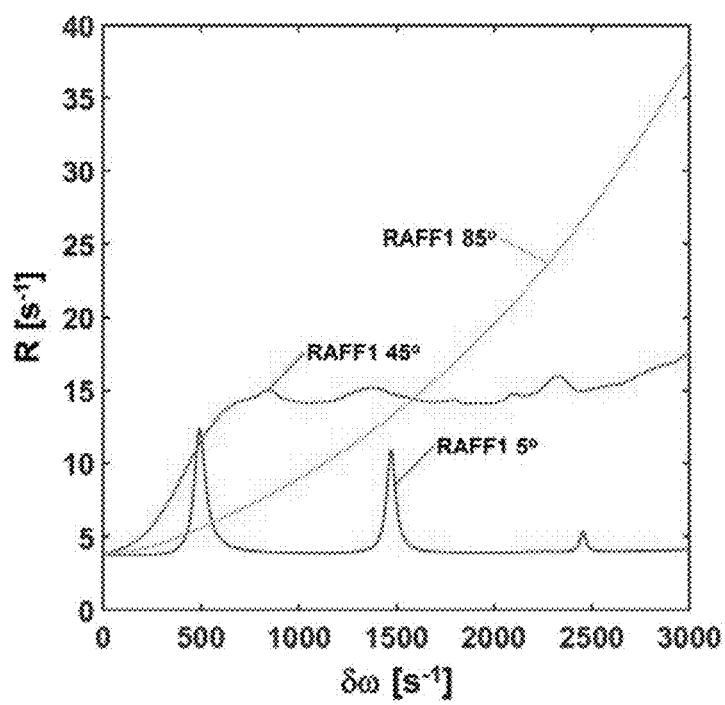
FIG. 4 is a graph of exchange-induced relaxation rate constants dependence on periodic irradiation according to some aspects of the present disclosure. The figure demonstrates change of the relaxation rate constant on $\alpha_1$ increases—the average flip angle in RAFF1, and therefore RAFF1 $\alpha_1$=5° (actual power 55 Hz) is more off-resonance $T_{1\rho}$ type measurement and RAFF1 $\alpha_1=85°$ (actual power 625 Hz) is more on-resonance $T_{2\rho}$ type measurement with refocusing.

Referring to FIG. 4, simulation of RAFF1 with different $\alpha_1$ angles demonstrates that an increase in relaxation rate constants correspond to a pulse sequence that generates sidebands. In some embodiments, the generation of sidebands occurs when the magnetization is close to the z-axis, i.e., when the $\alpha_1$ is relatively small (i.e., less than about 45°). The relaxation is boosted by a ratio of over 2 when the chemical shift δω between pools A and B is suitable for spin interaction. The simulation differs from conventional off-resonance spin-lock $T_{1\rho}$ simulation by the fact that magnetization starts from z-axis, precesses around the effective field, and due to refocusing, returns back to z-axis. When $\alpha_1$ increases, the ratio of $T_{2\rho}$ over the $T_{1\rho}$ also increases being almost solely $T_{2\rho}$ for $\alpha_1$=85°. For $\alpha_1$>45° the side bands were not observed using the simulation pulse sequence settings. When similar simulation is done for RAFF2 with the same $\alpha_1$, the results of the calculations with $\alpha_1$=5° and $\alpha_1$=85° are almost identical, which can be explained by the fact that magnetizations have similar average tip angle independently on difference in $T_{1\rho(n)}$ (alpha 5) or $T_{2\rho(n)}$ (alpha 85) contribution, and that magnetization is close to z-axis of the laboratory frame in both cases.

Figure 5:
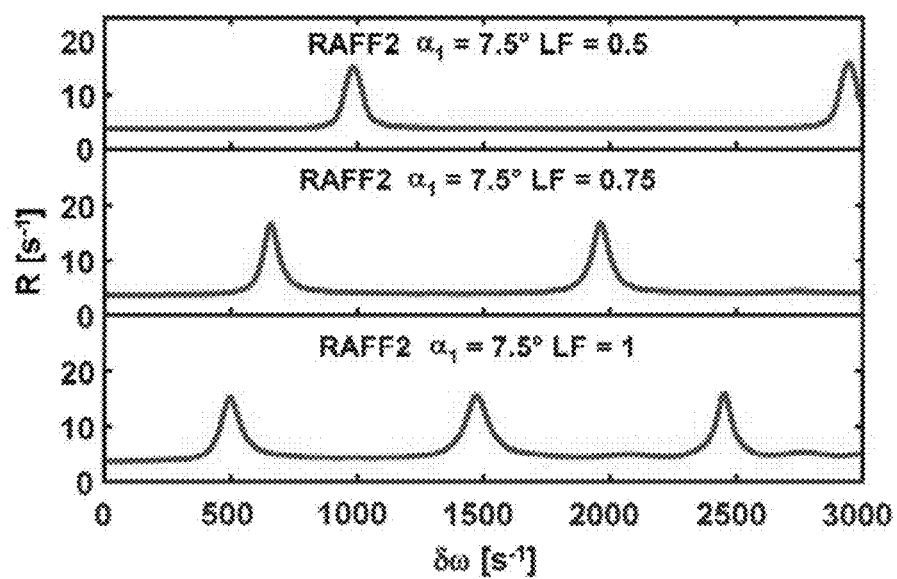
FIG. 5 are graphs of chemical exchange-induced relaxation rate constants dependence on the refocusing period of irradiation according to some aspects of the present disclosure. RAFF2 $PP_\pi^{-1}P_\pi P^{-1}$ packets are used with (top:) a length factor (LF) 0.5 resulting pulse duration of 1.1 ms and actual power of 97 Hz; (middle:) LF=0.75 resulting pulse duration of 1.7 ms and actual power of 142 Hz; and (bottom:) LF=1 to nominal RAFF2 pulse duration of 2.3 ms and actual power of 186 Hz. For simulations, exchange correlation time 10 ms, PA=0.1, and $\tau_c=76 \cdot 10^{-12}$ s for both sites are used. The length factor expands or cuts a RAFF waveform in duration by a scalar.

Referring to FIG. 5, analysis of the different durations of refocusing periods demonstrate that longer refocusing period leads to the relaxation rate peaks to move towards smaller $\delta\omega$ values. The pulse length $T_p$ is controlled by length factor (LF), which at the same time controls the refocusing time. The peaks of the rate constants correspond to $1/T_p$, i.e. for pulse length factor (LF)=1, to 2.3 ms, and similarly for the other LFs.

Figure 6:
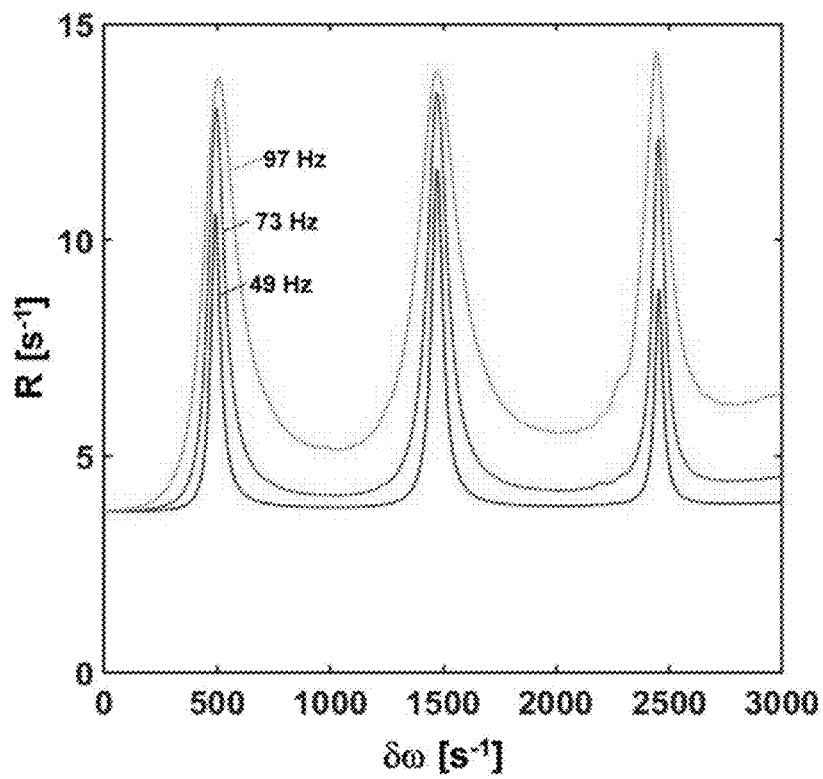
FIG. 6 is a graph of chemical exchange-induced relaxation rate constants dependence on RF power in accordance with some aspects of the present disclosure. RAFF2 $PP_\pi^{-1}P_\pi P^{-1}$ packets are used with a refocusing period of 2.3 ms, $\alpha_1=7.5°$, $\omega_1^{max}=625$ Hz. The pulse amplitude is multiplied by 0.5, 0.75, or 1 leading to actual pulse powers of 49, 73, and 97 Hz. For simulations, exchange correlation time 10 ms, PA=0.1, and $\tau_c=76 \cdot 10^{-12}$ s for both sites are used.

Referring to FIG. 6, exchange induced relaxation rate constants increase with an increasing RF power. Increase of the RAFF2 peak power without changing refocusing time leads to an increase of the average flip angle of M. Noticeably the locations of the side bands are independent of pulse power, however higher power settings lead to an increase of the relaxation rate constants.

Figure 7:
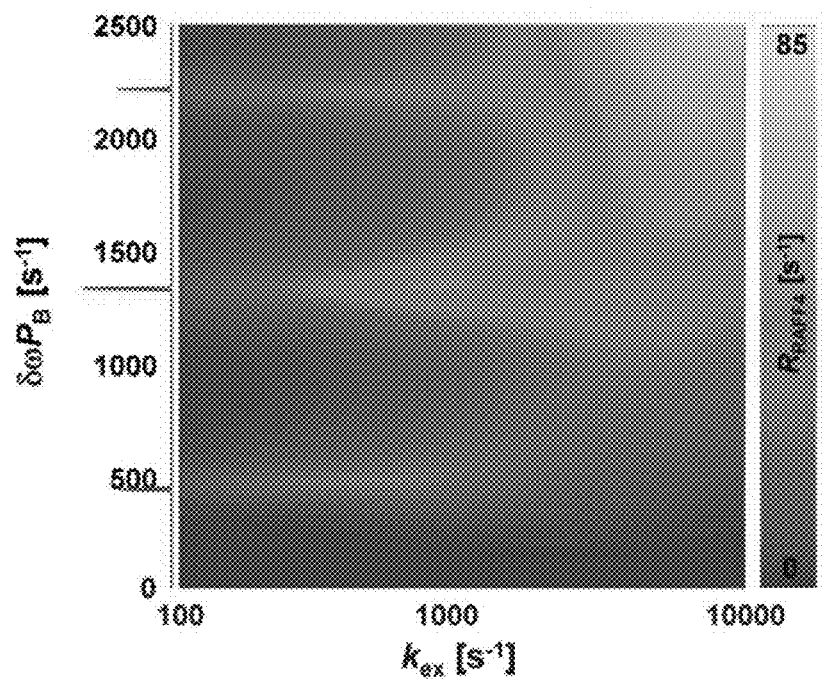
FIG. 7 is a two dimensional plot of exchange-induced relaxation rate constant versus chemical shift differences between exchanging sites A and B in accordance with some embodiments of the present disclosure. For the simulations RAFF4 45° pulses with $PP_\pi^{-1}P_\pi P^{-1}$ packets are used with refocusing period of 2.3 ms and with nominal $\omega_1^{max}=625$ Hz leading to actual pulse power of 140 Hz. $k_{ex}$ values are logarithmically distributed between 100 and 10000 $s^{-1}$ and 101 δω values are simulated between 0 and 3000 Hz with PA=0.1, and rotational correlation time for dipolar interactions $\tau_c=76 \cdot 10^{-12}$ s for both sites. After simulation, relaxation rate data is interpolated to 1024×1024 image points with bicubic interpolation. On the left, fast Fourier transform of RAFF4 45° pulse train in the form $\omega_1^{max}$ is shown in the frequency coordinates which is matched with the 2D plot.

Referring to FIG. 7, a contour plot of exchange induced relaxation rate constants during RAFF4 for different chemical shift differences and exchange correlation times is illustrated. FIG. 7 demonstrates that an increase of the exchange induced relaxation rate constant corresponds well with generation of side bands of the pulses when the instantaneous flip of the effective field occurs. Moreover, the enhanced rate constants at the side bands is observed for slow-to-intermediate exchange regimes, whereas when the system moves towards fast exchange limit, relaxation becomes very fast and enhancement at the side bands is not discernible any longer.

Figure 8:
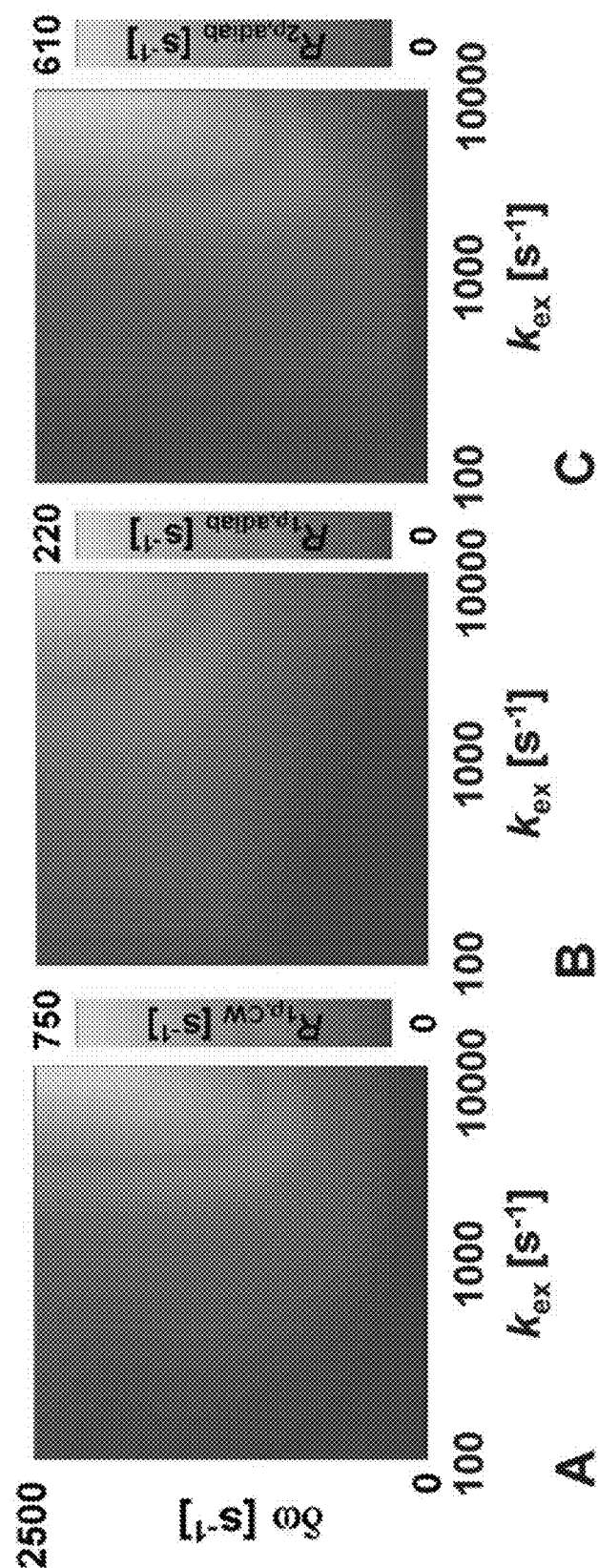
FIG. 8 is a two dimensional plot of exchange-induced relaxation rate constants versus chemical shift differences for exchanging sites A and B for: (A) conventional continuous wave $T_{1\rho}$, (B) adiabatic $T_{1\rho}$, and (C) adiabatic $T_{2\rho}$ simulation. For the simulations continuous wave (CW) (A) and Hyperbolic Secant (HS) pulses (B and C) are used. Peak power $\omega_1^{max}=625$ Hz (A) and 2500 Hz (B and C). Adiabatic pulse duration $T_p=4$ ms. Pulses are cycled according to MLEV-4. In adiabatic $T_{1\rho}$ magnetization is initially not perturbed, i.e., was along z'-axis of the first rotating frame. In adiabatic $T_{2\rho}$ magnetization is initially placed in the transverse plane. In all plots, $k_{ex}$ values are logarithmically distributed between 100 and 10,000 $s^{-1}$ and 101 δω values were simulated between 0 and 3000 Hz with PA=0.1, and $\tau_c=76 \cdot 10^{-12}$ s for both sites. After simulation, relaxation rate data is interpolated to 1024×1024 image points with bicubic interpolation.

Referring to FIG. 8, for comparison, the simulations of exchange induced relaxations during adiabatic $T_{1\rho}$, $T_{2\rho}$ and continuous wave spin lock $T_{1\rho}$ experiments are shown. In these comparison simulations, an increase of the relaxation rate constants was not observed. These further illustrates that using a frequency swept pulse sequence having amplitude and frequency modulated pulses and generating periodic irradiation by instantaneously flipping the effective field, allows for an enhancement of exchange induced relaxation rate constants which become discernible for small tip angle of magnetizations.

In some embodiments, the present disclosure demonstrates that an instantaneous flip of the effective field during rotating frame experiments leads to an increase of the exchange-induced relaxation rate constant. Numerical analysis of exchange-induced relaxation for two-site exchange during periodic irradiation leads to an increase of the relaxation rate constants which corresponds to the off-resonance side bands, and depends on the repetition rate of irradiation and the tip angle of magnetization. Simulations show that periodic irradiation produces sidebands in the chemical shift domain when the M remains only in one hemisphere, and the tip angle of M is relatively small, $\alpha_1$<45°. Furthermore, Bloch-McConnell simulation of RF pulses with different modulation functions of the RAFFn family demonstrate that for fixed average flip angles the position of side bands in chemical shift domain remains constant, independently from the pulse modulation functions. Moreover, the pulse amplitude does not influence the location of the sidebands while increasing the overall relaxation rate constants.

The methods presented herein offer important applications for studying exchanging systems in protein dynamics, and for detection of exchange—related processes in living samples. This methodology could serve as a sensitive non-invasive MRI tool for generating exchange-induced tissue contrast when selectively tuning to the chemical shifts of interest, and may compliment and even over perform established MRI modalities such as $T_2$- and $T_1$-weighted methods, other rotating frame and Chemical Shift Saturation Transfer (CEST) techniques.

Figure 9:
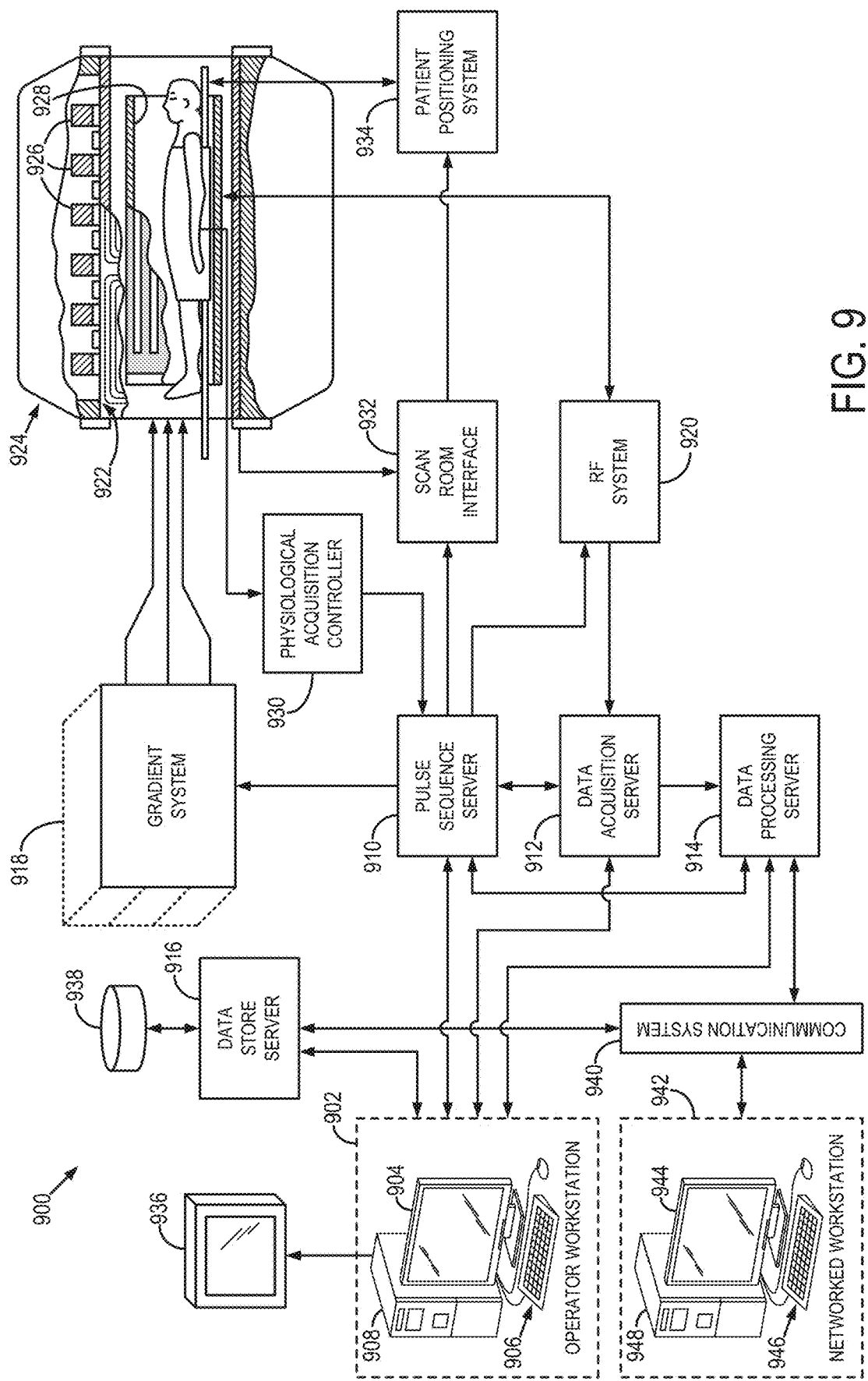
FIG. 9 is a block diagram of an example magnetic resonance imaging ("MRI") system that can implement methods described herein.

Referring particularly now to FIG. 9, an example of an MRI system 900 that can implement the methods described here is illustrated. The MRI system 900 includes an operator workstation 902 that may include a display 904, one or more input devices 906 (e.g., a keyboard, a mouse), and a processor 908. The processor 908 may include a commercially available programmable machine running a commercially available operating system. The operator workstation 902 provides an operator interface that facilitates entering scan parameters into the MRI system 900. The operator workstation 902 may be coupled to different servers, including, for example, a pulse sequence server 910, a data acquisition server 912, a data processing server 914, and a data store server 916. The operator workstation 902 and the servers 910, 912, 914, and 916 may be connected via a communication system 940, which may include wired or wireless network connections.

The pulse sequence server 910 functions in response to instructions provided by the operator workstation 902 to operate a gradient system 918 and a radiofrequency ("RF") system 920. Gradient waveforms for performing a prescribed scan are produced and applied to the gradient system 918, which then excites gradient coils in an assembly 922 to produce the magnetic field gradients $G_x$, $G_y$, and $G_z$ that are used for spatially encoding magnetic resonance signals. The gradient coil assembly 922 forms part of a magnet assembly 924 that includes a polarizing magnet 926 and a whole-body RF coil 928.

RF waveforms are applied by the RF system 920 to the RF coil 928, or a separate local coil to perform the prescribed magnetic resonance pulse sequence. Responsive magnetic resonance signals detected by the RF coil 928, or a separate local coil, are received by the RF system 920. The responsive magnetic resonance signals may be amplified, demodulated, filtered, and digitized under direction of commands produced by the pulse sequence server 910. The RF system 920 includes an RF transmitter for producing a wide variety of RF pulses used in MRI pulse sequences. The RF transmitter is responsive to the prescribed scan and direction from the pulse sequence server 910 to produce RF pulses of the desired frequency, phase, and pulse amplitude waveform. The generated RF pulses may be applied to the whole-body RF coil 928 or to one or more local coils or coil arrays.

The RF system 920 also includes one or more RF receiver channels. An RF receiver channel includes an RF preamplifier that amplifies the magnetic resonance signal received by the coil 928 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \tag{15}$$

and the phase of the received magnetic resonance signal may also be determined according to the following relationship:

$$\varphi = \tan^{-1}\left(\frac{Q}{I}\right). \tag{16}$$

The pulse sequence server 910 may receive patient data from a physiological acquisition controller 930. By way of example, the physiological acquisition controller 930 may receive signals from a number of different sensors connected to the patient, including electrocardiograph ("ECG") signals from electrodes, or respiratory signals from a respiratory bellows or other respiratory monitoring devices. These signals may be used by the pulse sequence server 910 to synchronize, or "gate," the performance of the scan with the subject's heart beat or respiration.

The pulse sequence server 910 may also connect to a scan room interface circuit 932 that receives signals from various sensors associated with the condition of the patient and the magnet system. Through the scan room interface circuit 932, a patient positioning system 934 can receive commands to move the patient to desired positions during the scan.

The digitized magnetic resonance signal samples produced by the RF system 920 are received by the data acquisition server 912. The data acquisition server 912 operates in response to instructions downloaded from the operator workstation 902 to receive the real-time magnetic resonance data and provide buffer storage, so that data is not lost by data overrun. In some scans, the data acquisition server 912 passes the acquired magnetic resonance data to the data processor server 914. In scans that require information derived from acquired magnetic resonance data to control the further performance of the scan, the data acquisition server 912 may be programmed to produce such information and convey it to the pulse sequence server 910. For example, during pre-scans, magnetic resonance data may be acquired and used to calibrate the pulse sequence performed by the pulse sequence server 910. As another example, navigator signals may be acquired and used to adjust the operating parameters of the RF system 920 or the gradient system 918, or to control the view order in which k-space is sampled. In still another example, the data acquisition server 912 may also process magnetic resonance signals used to detect and process magnetization data corresponding to at least one of the off resonance side bands. For example, the data acquisition server 912 may acquire magnetic resonance data and processes it in real-time to produce information that is used to control the scan.

The data processing server 914 receives magnetic resonance data from the data acquisition server 912 and processes the magnetic resonance data in accordance with instructions provided by the operator workstation 902. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 914 are conveyed back to the operator workstation 902 for storage. Real-time images may be stored in a data base memory cache, from which they may be output to operator display 902 or a display 936. Batch mode images or selected real time images may be stored in a host database on disc storage 938. When such images have been reconstructed and transferred to storage, the data processing server 914 may notify the data store server 916 on the operator workstation 902. The operator workstation 902 may be used by an operator to archive the images, produce films, or send the images via a network to other facilities.

The MRI system 900 may also include one or more networked workstations 942. For example, a networked workstation 942 may include a display 944, one or more input devices 946 (e.g., a keyboard, a mouse), and a processor 948. The networked workstation 942 may be located within the same facility as the operator workstation 902, or in a different facility, such as a different healthcare institution or clinic.

The networked workstation 942 may gain remote access to the data processing server 914 or data store server 916 via the communication system 940. Accordingly, multiple networked workstations 942 may have access to the data processing server 914 and the data store server 916. In this manner, magnetic resonance data, reconstructed images, or other data may be exchanged between the data processing server 914 or the data store server 916 and the networked workstations 942, such that the data or images may be remotely processed by a networked workstation 942.

Figure 10:
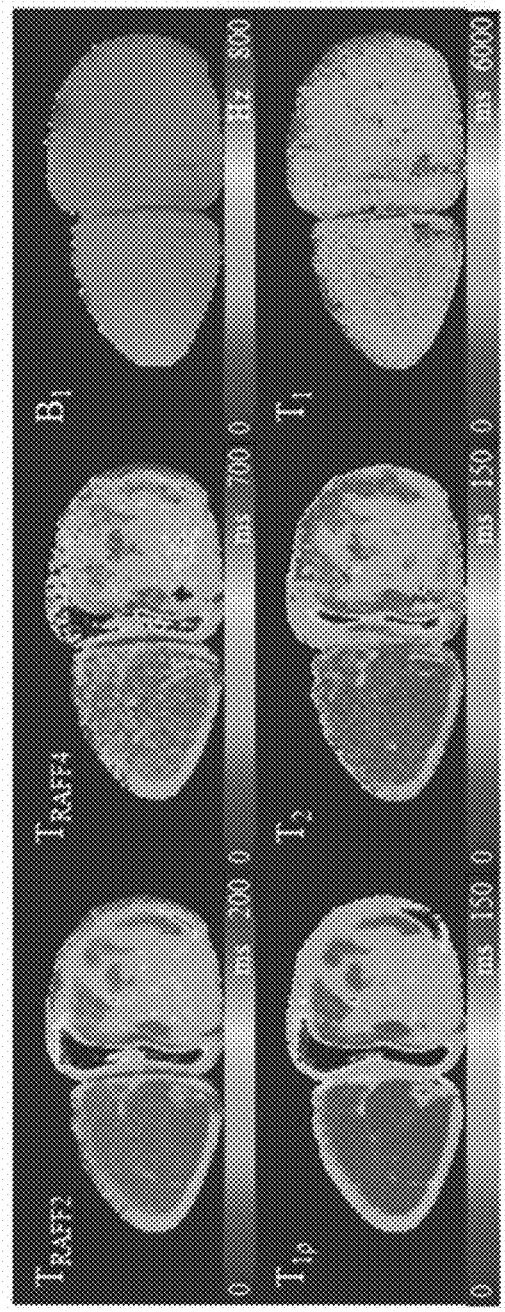
FIG. 10 is an image illustrating a representative example of RAFFn, and $T_{1\rho}$ compared to $T_1$ and $T_2$ relaxation time maps in mouse ischemic hind limb transversal section at 7 T.
Figure 11:
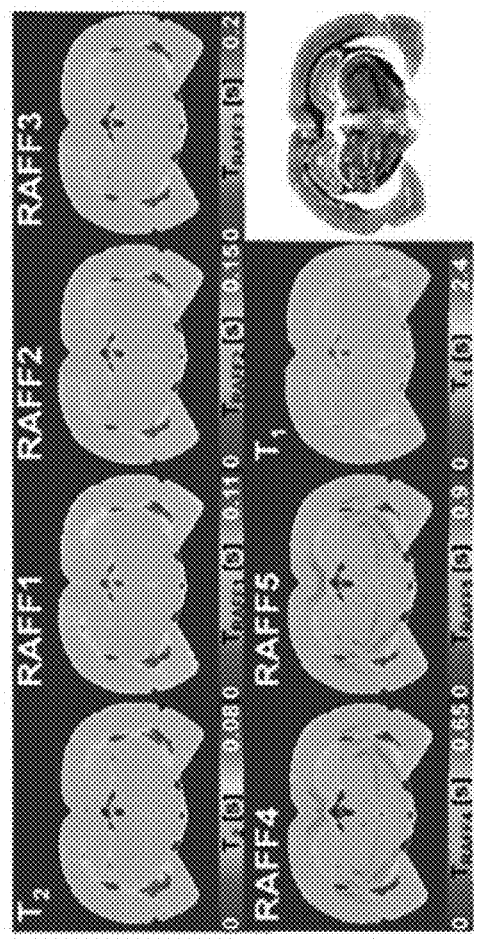
FIG. 11 is an image illustrating a comparison between RAFFn $T_2$ and $T_1$ in intact rat brain ex vivo at 9.4 T. Increase of n in RAFFn when ε=45° leads to increase of RAFF relaxation time, as well as, the increased contrast in the brain verified by Gold Chlorine stained histology, where darker tone of purple indicates more myelinated structures (white matter).

In some aspects, RAFFn provides greater flexibility for generation of relaxation contrasts non-invasively in MRI, and broadens the sensitivity of MR exam from fast to slow/ultra-slow motional regimes. In addition, the problem of SAR is substantially or completely resolved since it is significantly reduced at high rotating frames. The sensitivity of RAFFn to $B_0$ and $B_1$ inhomogeneities decreases, which is advantageous for practical measurements and clinical applicability. The contrast between grey and white matter in human and rat brains is found to increase with increased n at least up to n=5, and $T_{RAFF4}$ and $T_{RAFF5}$ exhibit great sensitivity to myelin content in rat models. RAFFn contrast differs from conventional T1 and T2, as well as, from CW, SL, $T_{1\rho}$ and adiabatic $T_{1\rho}$ and $T_{2\rho}$, as shown in FIGS. 10 and 11.

In some aspects, the measurements of relaxation times using conventional MRI techniques are typically time consuming. Several acceleration methods including parallel imaging and compressed sensing may be applied to speed up acquisition. In some aspects of the present disclosure, magnetic resonance fingerprinting ("MRF") may be utilized to speed up the acquisition of RAFFn.

MRF is a technique that facilitates mapping of tissue or other material properties based on random, pseudorandom, or otherwise varied measurements of the subject or object being imaged. In particular, MRF can be conceptualized as employing a series of varied "sequence blocks" that simultaneously produce different signal evolutions in different "resonant species" to which the RF is applied. The term "resonant species," as used herein, refers to a material, such as water, fat, bone, muscle, soft tissue, and the like, that can be made to resonate using NMR. By way of illustration, when radio frequency ("RF") energy is applied to a volume that has both bone and muscle tissue, both the bone and muscle tissue will produce a nuclear magnetic resonance ("NMR") signal; however, the "bone signal" represents a first resonant species and the "muscle signal" represents a second resonant species, and thus the two signals will be different. These different signals from different species can be collected simultaneously over a period of time to collect an overall "signal evolution" for the volume.

The random, pseudorandom, or otherwise varied measurements obtained in MRF techniques are achieved by varying the acquisition parameters from one repetition time ("TR") period to the next, which creates a time series of signals with varying contrast. Examples of acquisition parameters that can be varied include flip angle ("FA"), RF pulse phase, TR, echo time ("TE'), and sampling patterns, such as by modifying one or more readout encoding gradients. The acquisition parameters are varied in a random manner, pseudorandom manner, or other manner that results in signals from different materials or tissues to be spatially incoherent, temporally incoherent, or both. In some instances, the acquisition parameters can be varied according to a non-random or a non-pseudorandom pattern that otherwise results in signals from different materials or tissues to be spatially incoherent, temporally incoherent, or both.

From these measurements, MRF processes can be designed to map a wide variety of parameters that may be mapped individually or simultaneously. Examples of such parameters include, but are not limited to, longitudinal relaxation time ($T_1$), transverse relaxation time ($T_2$), main or static magnetic field map ($B_0$), and proton density (PD). Unlike conventional MR systems, tissue property maps may be generated simultaneously using MRF. Thus, rather than subjecting a patient to multiple serial acquisitions that may take a half hour or more, the patient may experience a much shorter time in the bore. Similarly, rather than making a radiologist wait for multiple images that are produced serially (e.g, a first pulse sequence to generate a $T_1$ map, a second pulse sequence to generate a $T_2$ map), the radiologist may be provided with maps that are produced simultaneously from the MRF data.

Examples of such parameters include, but are not limited to, longitudinal relaxation time ($T_1$) transverse relaxation time ($T_2$), main or static magnetic field map ($B_0$), and proton density (PD). MRF is generally described in U.S. Pat. No. 8,723,518 and Published U.S. Patent Application No. 2015/0301141, each of which is incorporated herein by reference in its entirety.

The signal evolutions that are acquired with MRF techniques are compared with a dictionary of signal models, or templates, that have been generated for different acquisition parameters from magnetic resonance signal models, such as Bloch equation-based physics simulations. The dictionary may also comprise a series of previously acquired known evolutions. This comparison allows estimation of the physical parameters, such as those mentioned above. As an example, the comparison of the acquired signals to a dictionary are typically performed using any a matching or pattern recognition technique. The parameters for the tissue or other material in a given voxel are estimated to be the values that provide the best signal template matching. For instance, the comparison of the acquired data with the dictionary can result in the selection of a signal vector, which may constitute a weighted combination of signal vectors, from the dictionary that best corresponds to the observed signal evolution. The selected signal vector includes values for multiple different quantitative parameters, which can be extracted from the selected signal vector and used to generate the relevant quantitative parameter maps.

The stored signals and information derived from reference signal evolutions may be associated with a potentially very large data space. The data space for signal evolutions can be partially described by:

$$SE = \sum_{s=1}^{N_S} \prod_{i=1}^{N_A} \sum_{j=1}^{N_{RF}} R_i(\alpha) R_{RF_{ij}}(\alpha, \phi) R(G) E_i(T_1, T_2, D) M_0; \quad (17)$$

where SE is a signal evolution; $N_S$ is a number of spins; $N_A$ is a number of sequence blocks; $N_{RF}$ is a number of RF pulses in a sequence block; $\alpha$ is a flip angle; $\phi$ is a phase angle; $R_i(\alpha)$ is a rotation due to off resonance; $R_{RF_{ij}}(\alpha,\phi)$ is a rotation due to RF differences; $R(G)$ is a rotation due to a magnetic field gradient; $T_1$ is a longitudinal, or spin-lattice, relaxation time constant; $T_2$ is a transverse, or spin-spin, relaxation time constant; D is diffusion coefficient; $E_i(T_1, T_2, D)$ is a signal decay; and $M_0$ is the initial magnetization.

While $E_i(T_1,T_1,D)$ is provided as an example, in different situations, the decay term, $E_i(T_1,T_2,D)$, may also include additional terms, $E_i(T_1,T_2,D, \ldots)$ or may include fewer terms, such as by not including the diffusion relaxation, as $E_i(T_1,T_2)$ or $E_i(T_1,T_2, \ldots)$. Also, the summation on "j" could be replaced by a product on "j".

The dictionary may store signals described by, $$S_i = R_i E_i(S_{i-1}) \quad (18)$$

where $S_0$ is the default, or equilibrium, magnetization; $S_i$ is a vector that represents the different components of magnetization, $M_x$, $M_y$, and $M_z$ during the $i^{th}$ acquisition block; $R_i$ is a combination of rotational effects that occur during the $i^{th}$ acquisition block; and $E_i$ is a combination of effects that alter the amount of magnetization in the different states for the $i^{th}$ acquisition block. In this situation, the signal at the $i^{th}$ acquisition block is a function of the previous signal at acquisition block (i.e., the $(i-1)^{th}$ acquisition block). Additionally or alternatively, the dictionary may store signals as a function of the current relaxation and rotation effects and of previous acquisitions. Additionally or alternatively, the dictionary may store signals such that voxels have multiple resonant species or spins, and the effects may be different for every spin within a voxel. Further still, the dictionary may store signals such that voxels may have multiple resonant species or spins, and the effects may be different for spins within a voxel, and thus the signal may be a function of the effects and the previous acquisition blocks.

Conventional MRF techniques rely on varying parameters, such as FA, RF pulse phase, TR, echo time ("TE'), and sampling patterns, to generate signal evolutions. In some aspects of the present disclosure, a rotating frame relaxation periodic irradiation method is presented. The method includes performing a pulse sequence having varied sequence blocks to acquire MRF data, where the sequence blocks vary from each other in one or more parameter including, but not limited to, n of RAFF from 1 to 5, ε angles from 1° and 89°, and a duration of P-packets (i.e., periodicity of irradiation) of RAFFn to alter the location of the sidebands.

In some aspects, the periodicity of irradiation ranges from 1 to 10 ms for proton MR. In some aspects, the periodicity of irradiation is at least 1 ms, or at least 2 ms, or at least 3 ms, or at least 4 ms, or at least 5 ms, or at least 6 ms, to less than 7 ms, or less than 8 ms, or less than 9 ms, or less than 10 ms.

In some aspects, the varied sequence blocks have exchanging site values (e.g., at least $P_A$ and $P_B$) that vary within the sequence block. In some aspects, the values vary from 0 to 1 within the sequence block.

In some aspects, the varied sequence blocks have chemical shift difference values between exchanging sites ($\Delta\omega$) that vary within the varied sequence block. In some aspects, the $\Delta\omega$ within the varied sequence blocks range from 1 ppm to 100 ppm. In some aspects, the $\Delta\omega$ within the varied sequence blocks range from at least 1 ppm, or at least 5 ppm, or at least 10 ppm, or at least 20 ppm, or at least 30 ppm, to less than 40 ppm, or less than 50 ppm, or less than 60 ppm, or less than 70 ppm, or less than 80 ppm, or less than 90 ppm, or less than 100 ppm.

In some aspects, the varied sequence blocks have exchange correlation times ($\tau_{ex}$) that vary within the varied sequence block. In some aspects, the $\tau_{ex}$ varies from microseconds to milliseconds.

Figure 12:
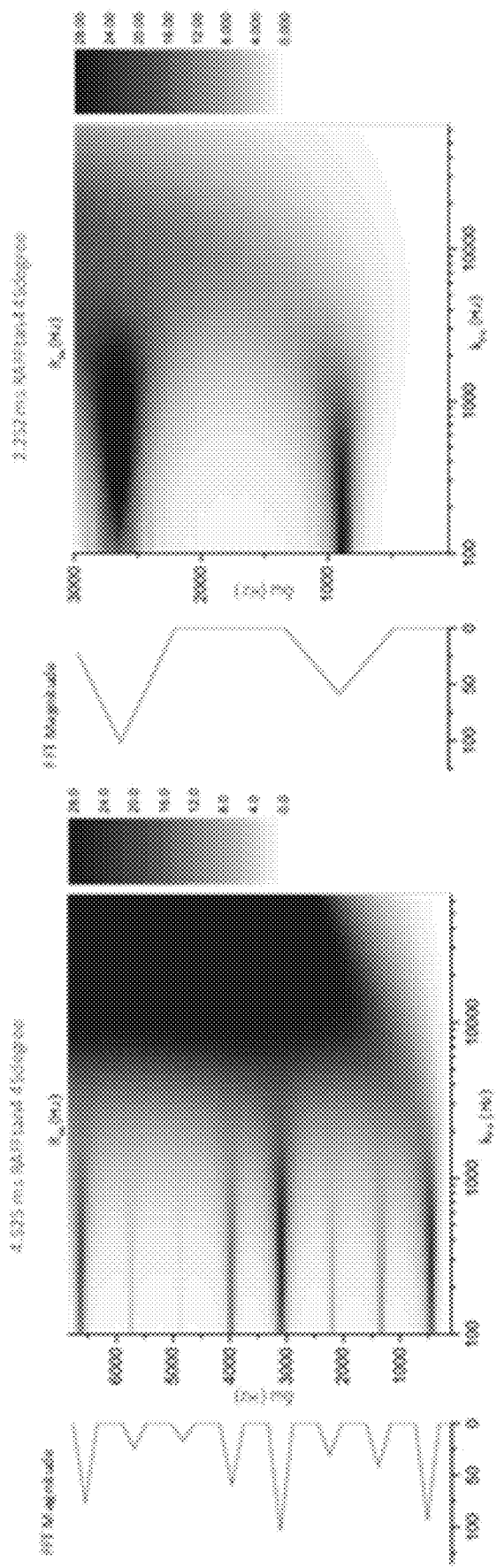
FIG. 12 are images of exchange induced relaxation rate constants for different durations of RAFF2 P-packets.

Because of instantaneous flip of the effective field which takes place several times during the P-packet, the periodicity of irradiation varies with the change of the duration of P-packet. As shown before in the case of RAFF2, the angle $\epsilon$ and the pulse duration at a given peak power affects the magnetization evolution during the pulse and the location of side bands in the chemical shift scale, which provides optimum signal variation for finger printing experiment and allows to probe exchanging system, as shown in FIG. 12.

Figure 13:
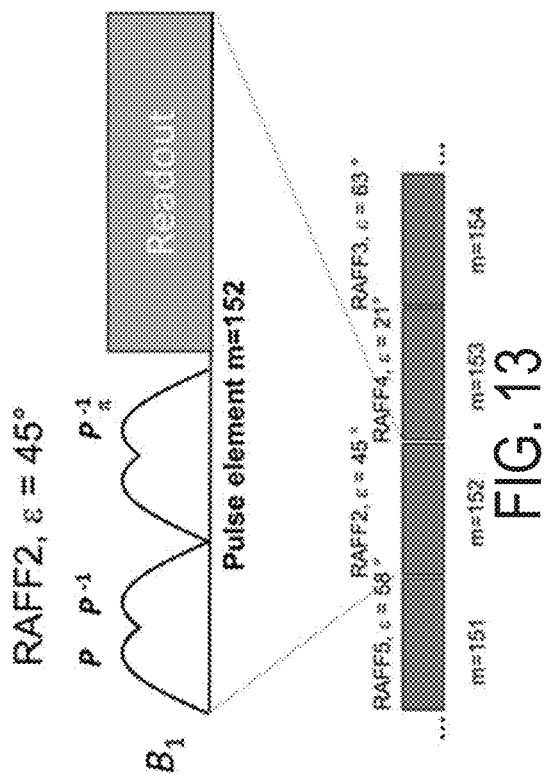
FIG. 13 is an illustration of an example rotating frame relaxation finger printing pulse sequence in accordance with some embodiments of the present disclosure.

FIG. 13 illustrates a non-limiting example of the rotating frame relaxation finger printing technique based on periodic irradiation. FIG. 13 shows a pulse sequence where n of RAFF is varied between 2 to 5 in each pulse element (m), where each pulse element has a random, pseudorandom, or otherwise varied $\epsilon$ angle. In some aspects, the pulse sequence includes a readout following each pulse element. In some aspects, one weighting combined with small flip angle readout forms the elements of the pulse sequence.

The basic elements are repeated hundreds of times m= [1, . . . , M] to produce temporarily unique signal for each set of fundamental molecular parameters. In some aspects, the pulse sequence includes a sufficient number of pulse elements to obtain unique signal evolutions for each set of desired parameters. In some aspects the pulse sequence includes from 1 to 1000 pulse elements, or more. In some aspects, the pulse sequence includes at least 10 pulse elements, or at least 100, or at least 200, or at least 300, or at least 400, or at least 500, to less than 600, or less than 700, or less than 800, or less than 900, or less than 1000 pulse elements.

Figure 14:
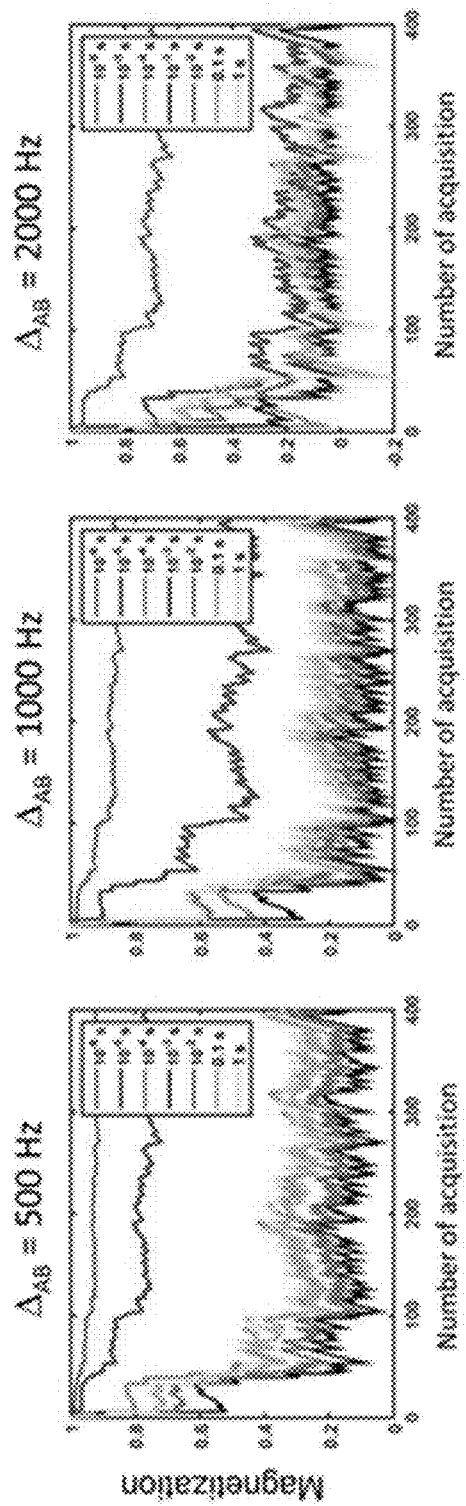
FIG. 14 are graphs of signal evolutions generated using a rotating frame relaxation finger printing pulse sequence in accordance with some embodiments of the present disclosure.

In some aspects, MRF dictionaries indicative of tissue signal behavior may be generated using Bloch McConnell equations, such as those described in equations (7)-(12). FIG. 14 illustrates signal evolutions generated using simulations where $\tau_c$ i.e. $T_1$ and $T_2$ of two pools were set identical and pool fraction $P_A$, $\tau_{ex}$, and $\Delta_{AB}$ varied. Referring to FIG. 14, example simulations are illustrated that generate signal evolutions with $\tau_{ex}=10^{-6}$ s to 1 s for different $\Delta_{AB}$ (different panels) when 400 repetitions are measured.

In some aspects, the rotating frame relaxation finger printing method includes comparing the MRF data acquired using the rotating frame relaxation finger printing method to a MRF dictionary in order to match the observed signal evolutions with the signal evolutions in the MRF dictionary. The step of comparing may be performed in a number of ways, such as a pattern or matching algorithm. The method further includes generating one or more tissue parameter or tissue property map of the region of interest. Non-limiting examples of tissue parameters and tissue property maps include relaxation parameters, tissue fractions, and proton density maps.

In some aspects, the images may be reconstructed pixel-by-pixel to generate an image. The reconstructed and acquired maps may be compared and error estimated by pixel-by-pixel manner. The parameter set may be used to generate or otherwise calculate parameters indicative of tissue in the region of interest, such as relaxation rates.

Figure 15:
FIG. 15 is a flowchart illustrating a non-limiting example method of performing the rotating frame relaxation finger printing pulse sequence in accordance with some embodiments of the present disclosure.
Figure 15:
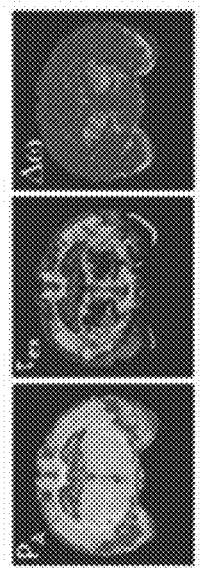

FIG. 15 illustrates a non-limiting example method of performing the rotating frame relaxation finger printing pulse sequence in accordance with some embodiments of the present disclosure. As shown, MRF data is acquired by varying RAFFn parameters, such as $P_A$, $\tau_{ex}$, $\Delta\omega$. The acquired MRF data is then compared to an MRF dictionary or library, which is generated using Bloch McConnell equations. In some aspects, the signal evolutions in the MRF data are then fit pixel-by-pixel to simulated signal evolutions in the MRF dictionary to identify a match between the simulated signals in the MRF dictionary and the acquired MRF data. Once a match is obtained, the selected signal evolution contains various quantitative parameters, which may be extracted and used to generate various parametric maps (e.g., $P_A$, $\tau_{ex}$, $\Delta\omega$), such as those illustrated in FIG. 15.

The present disclosure has described one or more preferred embodiments, and it should be appreciated that many equivalents, alternatives, variations, and modifications, aside from those expressly stated, are possible and within the scope of the invention.

The invention claimed is:

1. A method for acquiring a magnetic resonance (MR) data, the method including steps comprising:
applying periodic radiofrequency (RF) irradiation to a region of interest in a subject using a pulse sequence having frequency and amplitude modulate pulses to excite a spin system in the region of interest that includes at least a first labile spin species and a second labile spin species experiencing chemical exchange, wherein sweeping a frequency of the RF irradiation together with amplitude modulation generates a magnetic field component having an effective field;
generating off resonance side bands in a frequency domain positioned adjacent a resonant frequency of the first labile spin species or the second labile spin species by instantaneously flipping the effective field when applying the periodic RF irradiation;
acquiring magnetization data from the subject corresponding to at least one of the off resonance side bands.

2. The method of claim 1, wherein the magnetization data includes an exchange-induced relaxation rate.

3. The method of claim 1, wherein generating the off resonance side bands includes applying the periodic RF irradiation at a tip angle of magnetization of less than 45°.

4. The method of claim 1, wherein generating the off resonance side bands includes applying the periodic RF irradiation at a tip angle of magnetization between 0.1° and 30°.

5. The method of claim 1, wherein generating the off resonance side bands includes applying the periodic RF irradiation at a tip angle of magnetization between 5° and 15°.

6. The method of claim 1, wherein the RF irradiation is applied to the spin system such that the magnetization evolves in a positive hemisphere or a negative hemisphere without undergoing inversion.

7. The method of claim 1, wherein the RF irradiation is applied to the spin system such that the magnetization evolves without undergoing inversion, and wherein the periodic RF irradiation is applied at a tip angle of magnetization between of less than 45°.

8. The method of claim 1 further comprising selecting an irradiation period such that a frequency span of at least one of the off resonance side bands corresponds to a chemical shift difference between the first resonant species and the second resonant species.

9. The method of claim 1, wherein the frequency swept pulse sequence is configured to generate spin relaxation in the presence of the effective field in a second rotating frame of reference based on at least one magnetic field component that arises based on the effective field in a first rotating frame of reference, wherein the second rotating frame of reference is of higher order than the first rotating frame of reference.

10. The method of claim 9, wherein the frequency swept pulse sequence is configured to generate spin relaxation in the presence of a fictitious field in at least a third rotating frame of reference based on at least one magnetic field component that arises based on an effective field in the second rotating frame of reference relative to the first rotating frame of reference, wherein the third rotating frame of reference is of a higher order than the second rotating frame and the second rotating frame of reference is of a higher order than the first rotating frame of reference.

11. The method of claim 1, wherein the frequency swept pulse sequence is a hyperbolic secant pulse sequence having amplitude and frequency modulations.

12. A method for acquiring magnetization data using a magnetic resonance (MR) system, the method including steps comprising:
   applying periodic radiofrequency (RF) irradiation to a spin system in a region of interest in a subject using a frequency swept pulse sequence having frequency and amplitude modulation functions, wherein the frequency swept pulse sequence is configured to generate spin relaxation in the presence of a fictitious field in a second rotating frame of reference based on at least one magnetic field component that arises based on an effective field in a first rotating frame of reference, wherein the second rotating frame of reference is of a higher order than the first rotating frame of reference, and wherein each different rotating frame is associated with an effective field;
   generating off resonance side bands in a frequency domain positioned adjacent a resonant frequency of a first labile spin species in the spin system or a second labile spin species in the spin system by applying the periodic RF irradiation to induce an instantaneous flip of the effective field; and
   acquiring magnetization data from the region of interest corresponding to at least one of the off resonance side bands.

13. The method of claim 12, wherein the magnetization data includes an exchange-induced relaxation rate.

14. The method of claim 12, wherein generating the off resonance side bands includes applying the periodic RF irradiation at a tip angle of magnetization of less than 45°.

15. The method of claim 12, wherein the RF irradiation is applied to the spin system such that the magnetization evolves without undergoing inversion, and wherein the periodic RF irradiation is applied at a tip angle of magnetization between of less than 45°.

16. A method for acquiring magnetization data using a magnetic resonance (MR) system from a region of interest in a subject having a spin system that includes at least a first labile spin species and a second labile spin species experiencing chemical exchange, the method including steps comprising:
   applying periodic radiofrequency (RF) irradiation to the spin system using a frequency swept pulse sequence having frequency and amplitude modulation functions;
   generating off resonance side bands in a frequency domain positioned adjacent the resonant frequency of the first labile spin species or the second labile spin species by applying the periodic RF irradiation to induce an instantaneous flip of the effective field, and wherein an irradiation period of the RF irradiation is selected to correspond to a chemical shift difference between the first resonant species and the second resonant species; and
   acquiring magnetization data corresponding to at least one of the off resonance side bands.

17. The method of claim 16, wherein the magnetization data includes an exchange-induced relaxation rate constant.

18. The method of claim 16, wherein generating the off resonance side bands includes applying the periodic RF irradiation having a tip angle of magnetization that ranges between 5° and 45°.

19. The method of claim 16, wherein the frequency swept pulse sequence is configured to generate spin relaxation in the presence of a fictitious field in at least a second rotating frame of reference based on at least one magnetic field component that arises based on the effective field in a first rotating frame of reference, wherein the second rotating frame of reference is of higher order than the first rotating frame of reference.

20. The method of claim 16, wherein the frequency swept pulse sequence has amplitude and frequency modulations configured within a pulse sequence selected from a hyperbolic secant pulse sequence, a sine pulse sequence configured in a Relaxation Along a Fictitious Field in the rotating frame of rank n (RAFFn) sequence, or a cosine pulse sequence configured in a RAFFn sequence.

21. A method for generating a tissue property in a subject using magnetic resonance fingerprinting (MRF), the method comprising:
   acquiring MRF data from a region of interest in a subject by performing a pulse sequence having a series of varied sequence blocks to elicit signal evolutions, wherein the varied sequence blocks include a frequency swept or spin lock pulse sequence configured to generate spin relaxation in the presence of an effective field in a relaxation along a fictitious field in a rotating from of rank n (RAFFn), where n ranges from 2 to 5; and
   comparing the MRF data to an MRF dictionary to generate the tissue property from the region of interest.

* * * * *

UNITED STATES PATENT AND TRADEMARK OFFICE
CERTIFICATE OF CORRECTION

PATENT NO. : 11,474,174 B2
APPLICATION NO. : 17/008286
DATED : October 18, 2022
INVENTOR(S) : Shalom Michaeli et al.

It is certified that error appears in the above-identified patent and that said Letters Patent is hereby corrected as shown below:

In the Specification

Column 5, Line 24, "PA=0.1" should be --$P_A$=0.1--.

Signed and Sealed this
Twentieth Day of December, 2022

*Katherine Kelly Vidal*

Katherine Kelly Vidal
*Director of the United States Patent and Trademark Office*